United States Patent [19]

Parnell et al.

[11] Patent Number: 4,959,490

[45] Date of Patent: Sep. 25, 1990

[54] PROCESS FOR MANUFACTURING DISULFONATE SURFACTANTS

[75] Inventors: Margaret B. Parnell, Livermore, Calif.; Thomas L. Ashcraft, Jr., Baytown; Kenneth M. Webber, Houston, both of Tex.

[73] Assignee: Exxon Production Research Company, Houston, Tex.

[21] Appl. No.: 270,190

[22] Filed: Nov. 14, 1988

[51] Int. Cl.$^5$ .......................................... C07C 149/30
[52] U.S. Cl. ...................................................... 562/74
[58] Field of Search ............................................ 562/74

[56] References Cited

U.S. PATENT DOCUMENTS

| | | | |
|---|---|---|---|
| 2,106,716 | 2/1938 | Bruson | 260/99.12 |
| 2,143,759 | 1/1939 | Bruson et al. | 260/457 |
| 2,184,935 | 12/1939 | Bruson et al. | 260/512 |
| 3,393,221 | 7/1968 | Bochmke et al. | 260/465 |
| 3,721,707 | 3/1973 | Straus et al. | 260/513 |
| 4,293,428 | 10/1981 | Gale et al. | 252/8.55 |
| 4,426,303 | 1/1984 | Nuckels et al. | 252/8.55 |
| 4,588,534 | 5/1986 | Shepherd, Jr. et al. | 260/513 |

FOREIGN PATENT DOCUMENTS 1164889 4/1984 Canada .
WO88/03133 5/1988 World Int. Prop. O. .

OTHER PUBLICATIONS

Sulfonation Reactions, by E. Gilbert, 1965, pp. 297, 350, 378, and 379.
Gilbert, Sulfonation & Related Reactions (1965), p. 146.

*Primary Examiner*—Alan Siegel
*Attorney, Agent, or Firm*—Gary D. Lawson; Pamela L. Wilson

[57] ABSTRACT

A process for manufacturing monosulfonated alkylphenol polyalkylene oxide sulfonates is disclosed. The process produces the monosulfonated alkylphenol polyalkylene oxide sulfonates by a combination of sulfonation to produce a sulfate/sulfonate dianion, followed by a displacement of the sulfate to produce a disulfonate. The process produces a commercially viable disulfonate, which has a wide variety of commercial uses.

20 Claims, No Drawings

PROCESS FOR MANUFACTURING DISULFONATE SURFACTANTS

FIELD OF THE INVENTION

This invention relates to processes which may be used in the manufacture of disulfonate surfactant compounds. More particularly, this invention relates to synthesis of monosulfonated alkylphenol polyalkylene oxide sulfonates.

For the sake of brevity, the monosulfonate alkylphenol polyalkylene oxide sulfonates synthesized in accordance with this invention will sometimes be referred to herein as "APDS".

BACKGROUND OF THE INVENTION

It is known that several types of disulfonate surfactants exhibit high hydrophilicity and certain types have been suggested for use in detergent formulations and enhanced oil recovery operations.

One type of disulfonate surfactant is a diphenyl ether disulfonate, which is commercially available from the Dow Chemical Company under the trademark DOWFAX ®. These surfactants have the general formula:

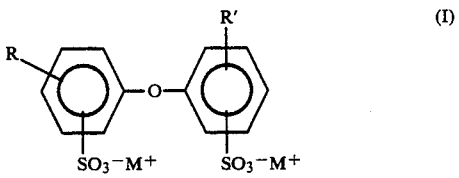
(I)

where R and R' are linear alkyl groups having 6 to 18 carbon atoms and each $M^{30}$ is a metal cation, where one of R or R' may be absent.

DOWFAX ® surfactants are manufactured by alkylation of diphenyl oxide with an olefin followed by direct sulfonation of each of the phenyl rings. The sulfonation can be carried out in an inert solvent, such as methylene chloride, using a sulfonating agent such as chlorosulfonic acid.

A second type of disulfonate is produced from an oxyalkylated alkylphenol. The general structure, which is disclosed in U.S. patent application Ser. No. 109,385 filed Oct. 15, 1987, by G. F. Teletzke et al., is shown below.

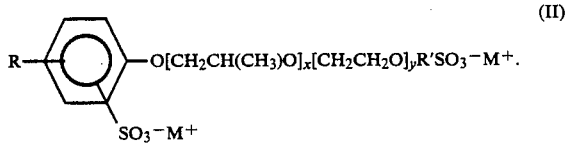
(II)

where
R is a linear or branched chain alkyl group with n carbon wherein n ranges from about 4 to about 30;
x ranges from 0 to about 20 and y ranges from 1 to about 50;
R' is a linear or branched chain alkyl group with m carbon atoms wherein m ranges from 1 to 4; and
each M+ is a cation.

The structure of this disulfonate is significantly different from that of the DOWFAX ® surfactants. For example, the surfactants of formula II contain an oxyalkyl chain that can be composed of repeating units of $C_2$ to $C_5$ alkenyl oxides (for example, ethylene oxide). Another major difference is that one of the sulfonate groups is attached at the terminal end of the oxyalkyl chain. The second sulfonate group is attached to the phenyl ring.

The oxyalkyl chain of formula II surfactants imparts hydrophilic or lipophilic properties that are not found in the DOWFAX ® surfactants. In addition, two or more alkenyl oxides can be incorporated into the oxyalkyl chain to provide structural combinations that provide a range of surfactant properties.

Previously proposed methods for preparing formula II surfactants have inherent drawbacks. One process involves the alkylation of phenol or methyl phenol followed by oxyalkylation. Propane sultone is then added to the terminus of the intermediate oxyalkyl alkyl phenol. This process requires the presence of a strong base, such as sodium metal or caustic, in an anhydrous aprotic solvent in order to get high yields of the monosulfonate. The monosulfonate is then reacted with chlorosulfonic acid, or other suitable sulfonating agent to add a sulfonate group to the phenyl ring. Under strong acid conditions the propanesulfonate group is easily removed, limiting the yield of the disulfonate. In addition, propane sultone is an expensive and hazardous reagent. This synthesis route cannot be adopted readily to a low-cost commercial process to manufacture APDS.

Another method of synthesizing formula II surfactants involves the use of allyl chloride adducts. In this procedure, allyl chloride is reacted with the terminus of the oxyalkyl chain in the presence of a strong base using an anhydrous aprotic solvent to form an allyl ether. The allyl ether is then reacted with chlorosulfonic acid, or some other suitable sulfonating agent, to add a sulfonate group to the phenyl ring. The final step is to form the second sulfonate group by addition of sodium bisulfite to the terminal olefin in an aqueous sulfite solution. This method is also comparatively expensive and disulfonate yields are low.

Still another method of synthesizing formula II surfactants involves converting the terminal hydroxyl group in the oxyalkyl alkylphenol chain to a chloride, sulfonating the phenol ring followed by displacing the chloride by sodium sulfite (Strecker reaction) in aqueous sodium sulfite. The limitations of this route are identical to those in the two methods mentioned above.

High disulfonate yields are important for many end uses of the disulfonate. Often with previously suggested synthesis routes, a large fraction of the product will have only one sulfonate group. Disulfonates containing a large fraction of monosulfonate would be undesirable for many applications that require a highly hydrophilic surfactant.

Moreover, methods suggested in the past for synthesizing ADPS will be inherently costly, involving expensive raw materials and processing.

SUMMARY OF THE INVENTION

The present invention is a novel method for producing a monosulfonated alkylphenol polyalkylene oxide sulfonate (APDS). The process involves alkylation of phenol or alkylphenols, such as methylphenol, with an olefin to form an alkylphenol. The alkylphenol is oxyalkylated with one or more $C_{2-5}$ alkenyl oxides to obtain the oxyalkyl alkylphenol having the desired alkenyl oxide(s) to alkylphenol mole ratios. The oxyalkylated alkylphenol is sulfonated with chlorosulfonic acid, sulfur trioxide, oleum or other suitable sulfonating agent to form a dianion sulfonate/sulfate characterized as follows:

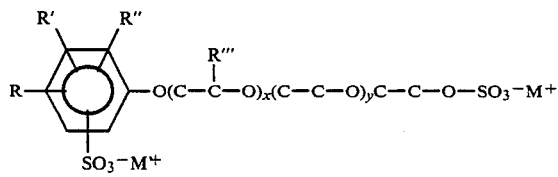

where
R is a linear or branched alkyl group having from 3 to about 40 carbon atoms;
R', R" and R''' are independently H or $C_{1-3}$ alkyl groups;
x ranges from 0 to about 10;
y ranges from 0 to about 50; and
each $M^+$ is a suitable cation.

The dianion will have a sulfate group attached to the terminus of the oxyalkylate chain and a sulfonate group directly attached to the phenyl ring.

The dianion is then reacted with an aqueous sulfite solution to displace the sulfate and replace it with a sulfonate. The structure of the disulfonate (APDS) is:

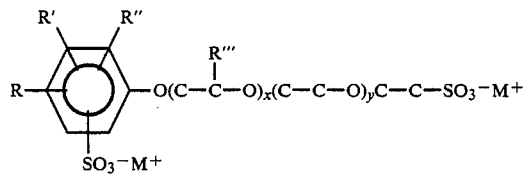

where the structural parameters are defined above.

DETAILED DESCRIPTION OF THE PREFERRED EMBODIMENT

In a preferred embodiment, a process is used which produces a commercially viable quantity of monosulfonated alkylphenol polyalkylene oxide sulfonate (APDS). The disulfonate has the general formula:

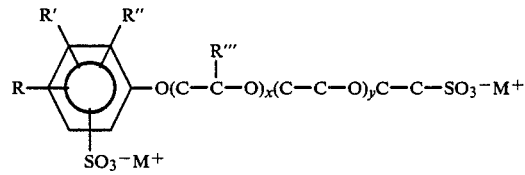

where
R is a linear or branched alkyl group having from 3 to about 40 carbon atoms;
R', R" and R''' are independently H or $C_{1-3}$ alkyl groups;
x ranges from 0 to about 10;
y ranges from 0 to about 50; and
each $M^{30}$ is a suitable cation comprising ammonia, amines, ethanolamines and metal mono- or di-cations.

The dianion will have one sulfonate group attached to the terminus of the dianion's oxyalkylate chain, and the other sulfonate group directly attached to the dianion's phenyl ring.

The first step of the process is the conventional alkylation of a phenol with a linear or branched olefin to form a linear or branched alkylphenol. This reaction may be characterized as follows:

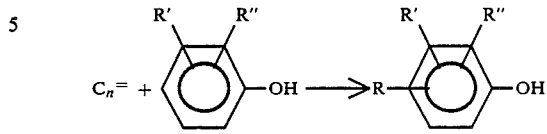

where
n is the number of carbon atoms and R,
R' and R" are the same as defined above.

The chain length of the olefin will be chosen to optimize the properties of the target surfactant for the anticipated application. This reaction typically takes place in the presence of a catalyst such as boron trifluoride etherate. The mole ratio of phenol to olefin is preferably 1:1 to 10:1 and more preferably 2:1 to 6:1. The reaction will proceed at temperatures of 0° C. to 200° C., with a preferred range of 60° C. to 150° C. Suitable alkylphenols are also commercially available from a variety of manufacturers.

The alkylphenol is then conventionally oxyalkylated with one or more low molecular weight alkylene oxides. Suitable alkylene oxides include ethylene oxide, propylene oxide and butylene oxide. However, any alkylene oxide adducted to the end of the oxyalkylate chain must have a primary alcohol functionality. For this reason, ethylene oxide is the preferred alkylene oxide for use in this reaction. The mole ratio of total alkylene oxide to alkylphenol should be 1:1 to 100:1, and more preferably 1.1:1 to 30:1. The reaction temperature should be 100° C. to 200° C., with a preferred temperature of between 125° C. and 150° C. A small amount of catalyst such as a potassium cation is preferably present during the reaction.

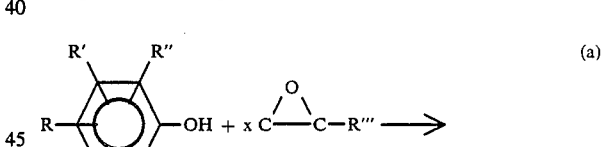
(a)

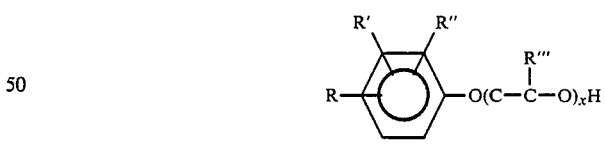
(b)

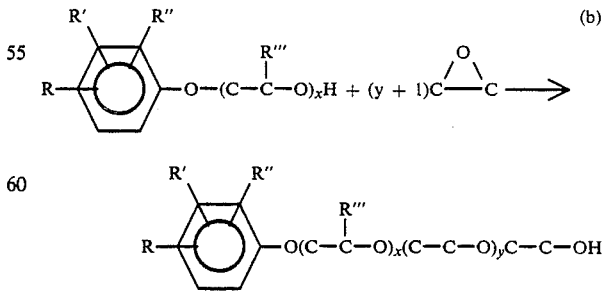

The oxyalkylated alkylphenol is then sulfonated using a suitable sulfonating agent such as chlorosulfonic acid, $SO_3$, or oleum.

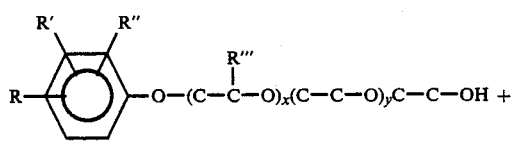

$$2[SO_3] \longrightarrow$$

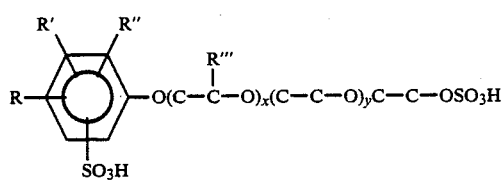

where
- R is a linear or branched alkyl group having from 3 to about 40 carbon atoms;
- R', R" and R'" are independently H or $C_{1-3}$ alkyl groups;
- x ranges from 0 to about 10; and
- y ranges from 0 to about 50.

In order for the process to be commercially feasible, yields of the dianion preferably exceed about 80–85 mole % based on the starting alkylphenol.

High yields of sulfate/sulfonate diacid can be obtained by reacting the oxyalkylated alkylphenol with chlorosulfonic acid. The mole ratio of chlorosulfonic to oxyalkylated alkylphenol is preferably 1.9:1 to 3:1, and more preferably 2:1 to 2.5:1. The reaction, which is strongly exothermic, may be carried out at temperatures of $-20°$ C. to 75° C., and preferably 0° C. to 40° C.

Sulfonation may also be accomplished by reacting the oxyalkylated alkylphenol with gaseous sulfur trioxide ($SO_3$). While yields of sulfate/sulfonate diacid are generally not as high as with chlorosulfonic acid, the use of $SO_3$ requires less investment and has lower operating costs. The mole ratio of gaseous $SO_3$ to oxyalkylated alkylphenol is preferably 1.9:1 to 2.5:1, and more preferably 2.0:1 to 2.2:1. The reaction temperature should be 30° C. to 120° C., with a preferred range of 50° C. to 90° C.

The diacid is then conventionally neutralized with any standard base, such as sodium hydroxide, potassium hydroxide, a sodium sulfite, a sodium carbonate, ammonia, or an ethanol amine to form a neutral dianion salt. The base is selected on the basis of cost, availability and performance.

The final step is the replacement of the sulfate from the terminus of the dianion's oxyalkylate chain with a sulfonate. The neutralized dianion is reacted with an aqueous sulfite solution (e.g. sodium sulfite). The ratio of sulfite to dianion should be in the range of 1:1 to 10:1 moles per mole and more preferably in the range of 2:1 to 6:1. The reaction temperature may be 100° C. to 250° C., with a preferred temperature of 120° C. to 200° C. The final product, a monosulfonated alkylphenol polyalkylene oxide sulfonate (APDS), is formed in this reaction. The disulfonate has the general formula:

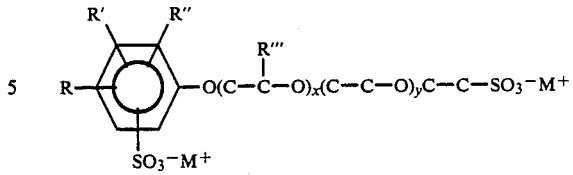

where
- R is a linear or branched alkyl group having from 3 to about 40 carbon atoms;
- R', R" and R'" are independently H or $C_{1-3}$ alkyl groups;
- x ranges from 0 to about 10;
- y ranges from 0 to about 50; and
- each $M^+$ is a suitable cation comprising ammonia, amines, ethanolamines and metal mono- or dications.

The disulfonate is then separated from the aqueous solution containing both inorganic salts and unreacted sulfite by extraction with butanol or other low molecular weight oxygenated organic solvents. The ability to effectively concentrate the disulfonate is advantageous in reducing costs for transporting the disulfonate products. In addition, the unreacted sulfite can be recycled for use in subsequent displacement reactions. The organic solvent can also be recycled and reused in the extraction step.

The combination of sulfonation of the oxyalkylated alkylphenol and subsequent displacement of the sulfate by use of a sulfite is a novel method for producing a monosulfonated alkylphenol polyalkylene oxide sulfonate.

The following examples demonstrate the effectiveness of this process in producing high yields of monosulfonated alkylphenol polyalkylene oxide sulfonate.

EXAMPLE 1

In a glass reaction vessel, 44.6 mole (4196 g) of phenol, 7.4 mole (1667 g) of commercially available linear $C_{16}$ alpha-olefin, and 1.2 mole (167 g) of boron trifluoride etherate were reacted at 80°–90° C. for two hours. Hexadecyl phenol was recovered by distillation. About 1.9 mole (615 g) of the hexadecylphenol were combined with 0.04 mole (2 g) of potassium hydroxide in a pressure reactor and stripped with dry nitrogen for 16 hours to remove water. The mixture was heated to 125° C.–140° C. and 2.1 mole (94 g) of ethylene oxide was added. The combination was allowed to react for about four hours, with a recovery of about 1.9 mole (708 g) of ethoxylated alkylphenol.

About 0.33 mole (120 g) of the ethoxylated alkylphenol was placed in a glass reaction vessel with 240 g dry dichloromethane solvent. The reaction vessel was cooled to 5° C. 0.73 mole (120 g) of chlorosulfonic acid was added dropwise during a 20-30 minute period. The temperature was maintained below 35° C. After addition of the chlorosulfonic acid, the product mixture was allowed to digest for 15–20 minutes. Then the dichloromethane was stripped from the product using standard laboratory vacuum evaporator equipment.

Approximately 0.33 mole (173 g) of the dianionic ethoxy alkylphenol sulfate/sulfonate diacid was recovered. At this point, spectra obtained from conventional High Performance Liquid Chromatographic (HPLC) analyses of the liquid sulfonation product indicated that 90-95 percent of the ethoxylated alkylphenol was converted to the sulfate/sulfonate diacid (a sulfonate group on the phenyl ring and a sulfate group attached to the terminus of the oxyalkyl chain).

The diacid was then neutralized with 0.73 mole of sodium hydroxide to form a dianionic salt. About 0.05 mole (30 g) of the dianionic salt was reacted with 0.18 mole of sulfite (18 g $Na_2SO_3$ and 4 g $NaHSO_3$ dissolved in 130 g of water). The reaction mixture was heated to 176° C. for 16 hours. The resulting APDS was extracted with 15 g of n-butanol. HPLC analyses showed that 58 percent of the sulfate on the oxyalkyl chain of the dianion was converted to sulfonate. Based on the initial molar amount of ethoxy alkylphenol, 53 percent of the desired disulfonate was recovered.

EXAMPLE 2

About 5.8 mole (1515 g) of commercially available isododecyl phenol was mixed with 33.9 mole (1492 g) of ethylene oxide and 0.17 mole (12 g) of potassium methoxide. The mixture was heated to 144° C. and allowed to react for about two hours. About 5.4 mole (2810 g) of ethoxylated alkylphenol was recovered after filtration.

About 0.19 mole (110 g) of the ethoxylated alkylphenol was placed in a glass reaction vessel with 200 g of dichloromethane solvent and the vessel was cooled to 0° C. 0.43 mole (50.2 g) of chlorosulfonic acid was added dropwise. The temperature was allowed to rise from 0° C. to 40° C. Approximately 0.19 mole (129 g) of the dianionic ethoxy alkylphenol sulfate/sulfonate diacid was recovered after solvent stripping.

The sulfate/sulfonate diacid was mixed with 58 g of 50% sodium hydroxide to form a sulfate/sulfonate dianionic salt. About 0.05 mole (33 g) of the dianionic salt was reacted with 0.23 mole of a solution containing 24 g $Na_2SO_3$ and 5 g $NaHSO_3$ dissolved in 95 g water. The reaction took place at 196° C. for two hours. The resulting monosulfonated alkylphenol polyalkylene oxide sulfonate was extracted with 18 g of n-butanol. Conventional HPLC analyses showed that 84 percent of the sulfate from the sulfate/sulfonate dianionic salt was converted to the sulfonate.

EXAMPLE 3

About 0.83 mole (182 g) of commercially available isononyl phenol was mixed with 5 mole (218 g) of ethylene oxide and 0.02 mole (1.5 g) of potassium methoxide. The mixture was heated to 144° C. and allowed to react for one hour. About 0.8 mole (393 g) of ethoxylated alkylphenol was recovered following filtration of the raw ethoxylation product.

About 0.21 mole (100 g) of the ethoxylated nonylphenol was reacted with 0.45 mole (53.1 g) of chlorosulfonic acid in 200 g of dichloromethane solvent. The chlorosulfonic acid was added dropwise after the reaction mixture was cooled to 0° C. After the addition of the chlorosulfonic acid was completed, the reaction mixture was allowed to rise to 40° C. to complete the reaction of any residual chlorosulfonic acid. Approximately 0.21 mole (135 g) of the dianionic ethoxy nonylphenol sulfate/sulfonate diacid was recovered on removal of the solvent.

The sulfate/sulfonate diacid was neutralized with 34 g of 50% sodium hydroxide to form a sulfate/sulfonate dianionic salt. About 0.03 mole (20 g) of the dianionic salt was reacted with 0.15 mole of sulfite (14 g $Na_2SO_3$ and 3 g $NaSO_3$ dissolved in 70 g of water). The mixture was heated to 196° C. and allowed to react for 2 hours. The APDS was extracted with butanol. HPLC spectra confirmed that 89% of the sulfate from the sulfate/sulfonate dianionic salt had been converted to the sulfonate.

EXAMPLE 4

About 59.2 mole (5560 g) of phenol and 2.25 mole (330 g) of boron trifluoride etherate were added to a reaction flask and heated to 80° C. 14.8 mole (3315 g) of commercially available linear $C_{16}$ alpha olefin was added dropwise to the reacting mixture. The temperature was maintained between 80° C. and 90° C. The mixture was allowed to react for one hour after the addition of the olefin was completed. 500 ml aliquots of water was used to extract the catalyst from the hexadecylphenol product. The raw alkylation product was dried and distilled using conventional laboratory glass vacuum distillation apparatus. About 13.2 mole (4200 g) of hexadecylphenol was recovered, of which 7-8% was (dihexadecyl) phenol.

6.2 mole (1969 g) of the hexadecylphenol and 0.2 mole (25 g) of 50% potassium hydroxide were charged to an autoclave and stripped with dry nitrogen for 16 hours to remove water. 33.1 mole (1460 g) of ethylene oxide was added to the reactor. The temperature was maintained between 129° C. and 141° C. during the reaction. The temperature was then increased to 149° C. for one hour. The ethoxy hexadecylphenol product was filtered and stripped with nitrogen to remove low molecular weight volatile components.

The ethoxy hexadecylphenol was fed to a continuous falling film reactor at four different rates between 0.0398 mole/minute and 0.0582 mole/minute. Liquid sulfur trioxide was fed to a heated evaporator at a constant rate of 0.0875 mole/minute (7.0 g/min) where the $SO_3$ was evaporated into a stream of dry nitrogen (2.1 mole/min) to achieve a concentration of 4.0 mole percent $SO_3$. This stream was contacted with the ethoxy hexadecylphenol at the inlet of the falling film reactor. The dianionic ethoxy hexadecylphenol sulfate/sulfonate diacid was separated from the nitrogen gas and collected. The $SO_3$/ethoxy hexadecylphenol mole ratios were 1.5, 1.8, 2.0 and 2.2 mole/mole. HPLC spectra of the sulfate/sulfonate diacid product indicated that between 50 and 55 percent of the ethoxy hexadecylphenol was converted to the diacid. 5% of the ethoxy hexadecylphenol was unreacted, and 40 to 45 percent of the ethoxy alkylphenol was converted to a mixture of ether sulfate and ethoxylated mono ring sulfonate.

The invention teaches a novel technique to produce APDS with yields of disulfonate greater than 80 mole % based on the starting alkylphenol. This procedure may be readily applied using existing commercial facilities.

A specific embodiment of the invention has been illustrated and described above. Modifications of the above embodiment may be suggested to persons skilled in the art and it is intended that this patent application cover all such modifications that fall within the scope of the attached claims.

We claim:

1. A process for synthesizing monosulfonated alkylphenol polyalkylene oxide sulfonates having the general formula:

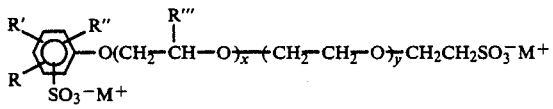

where
R is a linear or branched alkyl group having from 3 to about 40 carbon atoms;
R', R" and R'" are independently H or $C_{1-3}$ alkyl groups;
x ranges from 0 to about 10;
y ranges from 0 to about 50; and
each $M^+$ is a cation;
comprising the steps of:
(a) reacting an alkylphenol with alkylene oxide in an oxyalkylation reaction to produce an oxyalkylated alkylphenol including an oxyalkylate chain;
(b) reacting said oxyalkylated alkylphenol with a sulfonating reagent to produce a sulfonic/sulfate acid dianion having a sulfate group attached at the terminus of the said oxyalkylate chain and a sulfonate group attached to the phenol ring;
(c) reacting said sulfonic/sulfate acid dianion with a neutralizing agent to produce a dianion salt having a neutralized sulfate and a neutralized sulfonate group; and
(d) reacting said dianion salt with an agent capable of displacing said sulfate group with a sulfonate group to produce said monosulfonated alkylphenol polyalkylene oxide sulfonate; and
(e) extracting said monosulfonated alkylphenol polyalkylene oxide sulfonate with a low molecular weight oxygenated organic solvent.

2. The process of claim 1 wherein said alkylene oxide is reacted with said alkylphenol in a mole ratio of from 1:1 to 100:1.

3. The process of claim 1 wherein said alkylene oxide is reacted with said alkylphenol in a mole ratio of from 1.1:1 to 30:1.

4. The process of claim 1 wherein said alkylene oxide is ethylene oxide.

5. The process of claim 1 wherein said sulfonating agent is sulfur trioxide.

6. The process of claim 5 wherein said sulfur trioxide is reacted with said oxyalkylated alkylphenol in a mole ratio of from 1.9:1 to 2.5:1.

7. The process of claim 5 wherein said sulfur trioxide is reacted with said oxyalkylated alkylphenol in a mole ratio of from 2.0:1 to 2.2:1.

8. The process of claim 1 wherein said sulfonating reagent is chlorosulfonic acid.

9. The process of claim 8 wherein said chlorosulfonic acid is reacted with said oxyalkylated alkylphenol in a mole ratio of from 1.9:1 to 3:1.

10. The process of claim 8 wherein said chlorosulfonic acid is reacted with said oxyalkylated alkylphenol in a mole ratio of from 2:1 to 2.5:1.

11. The process of claim 1 wherein said sulfonating agent is oleum.

12. The process of claim 1 wherein said agent capable of displacing said sulfate group is a sulfite salt.

13. The process of claim 1 wherein said dianion salt is reacted with said sulfite salt in a mole ratio of from 1:1 to 10:1.

14. The process of claim 13 wherein said dianion salt is reacted with said sulfite salt in a mole ratio of from 2:1 to 6:1.

15. The process of claim 1 wherein said agent capable of displacing said sulfate group with a sulfonate group is an aqueous solution.

16. The process of claim 15 wherein said organic solvent is butanol.

17. A process for the manufacture of monosulfonated alkylphenol polyalkylene oxide sulfonates having the general formula:

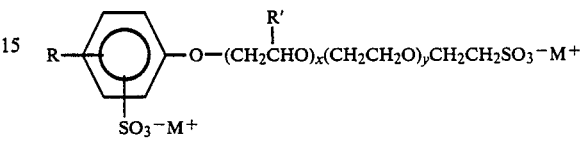

where
R is a linear or branched alkyl group including from 3 to 40 carbons;
R' is H, $CH_3$ or $CH_2CH_3$;
x ranges from 0 to about 10;
y ranges from 0 to about 50; and
each $M^+$ is a metal cation;
comprising the steps of:
(a) reacting a phenol with an olefin in an alkylation process to produce an alkylphenol;
(b) reacting an alkylphenol with alkylene oxide in an alkoxylation process to produce an oxyalkylated alkylphenol including an oxyalkylate chain;
(c) reacting said oxyalkylated alkylphenol with a sulfonating compound to produce a dianionic oxyalkylated alkylphenol having a sulfate group attached at the terminus of said oxyalkylate chain group and a sulfonate group attached to the phenyl ring;
(d) reacting said dianionic oxyalkylated alkylphenol with a neutralizing agent to produce a dianionic oxyalkylated alkylphenol having a neutralized sulfate group and a neutralized sulfonate group; and
(e) reacting said neutralized dianionic oxyalkylated alkylphenol with an agent capable of displacing said sulfate group with a sulfonate group to produce said monosulfonated alkylphenol polyalkylene oxide sulfonate; and
(f) extracting said monosufonated alkylphenol polyalkylene oxide sulfonate with a low molecular weight oxygenated organic solvent.

18. The process of claim 17 wherein said phenol is reacted with said olefin in a mole ratio of from 1:1 to 10:1.

19. The process of claim 18 wherein said phenol is reacted with said olefin in a mole ratio of from 2:1 to 6:1.

20. A process for the manufacture of monosulfonated alkylphenol polyalkylene oxide sulfonates having the general formula:

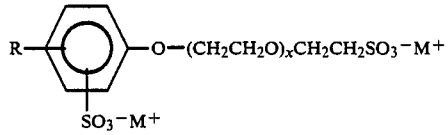

wherein R is a linear or branched alkyl group including from 3 to 40 carbons, x from 1 to about 10, each M+ is a metal cation, comprising the steps of:

(a) reacting an alkylphenol with ethylene oxide in an ethoxylation process to produce an ethoxy alkylphenol including an ethoxy chain;

(b) reacting said ethoxy alkylphenol with a sulfonating compound to produce a dianionic ethoxy alkylphenol having a sulfate group attached at the terminus of said ethoxy chain group and a sulfonate group attached to the phenyl ring;

(c) reacting said dianionic ethoxy alkylphenol with a neutralizing agent to produce a dianionic ethoxy alkylphenol having a neutralized sulfate group and a neutralized sulfonate group;

(d) reacting said neutralized dianionic ethoxy alkylphenol with a sulfite to produce said monosulfonated alkylphenol polyalkylene oxide sulfonate; and (e) extracting said monosulfonated alkylphenol polyalkylene oxide sulfonate with a low molecular weight oxygenated organic solvent.

* * * * *